United States Patent [19]

Day et al.

[11] 3,959,351

[45] May 25, 1976

[54] HALOALKYLBENZOYL ESTERS OF DI-LOWER ALKYLAMINO ALKANOLS AND QUATERNARY LOWER ALKYL SALTS THEREOF

[75] Inventors: Richard A. Day, Cleves; Rasikkumar N. Gohil, Cincinnati, both of Ohio

[73] Assignee: Research Corporation, New York, N.Y.

[22] Filed: July 24, 1972

[21] Appl. No.: 274,716

[52] U.S. Cl............................ 260/477; 260/544 D; 424/308
[51] Int. Cl.² .................................... C07C 93/20
[58] Field of Search ................................. 260/477

[56] References Cited
UNITED STATES PATENTS 3,794,677    2/1974    Bruce................................ 260/477

OTHER PUBLICATIONS

Z. Atare, et al., Latr. PSR Zinat. Akad. Vestis 1967(8) 111–116 (Russ).

*Primary Examiner*—Anton H. Sutto
*Assistant Examiner*—Paul J. Killos
*Attorney, Agent, or Firm*—Behr & Woodbridge

[57] ABSTRACT

There are provided certain novel halo lower alkyl benzoyl esters of di(lower alkyl amino) lower alkanols and the quaternary salts thereof, in particular the bromomethyl benzoyl esters of dimethyl aminoethanol and choline which possess activity as insecticides and cholinesterase inhibitors. The corresponding formyl benzoyl esters exhibit similar activity.

9 Claims, No Drawings

HALOALKYLBENZOYL ESTERS OF DI-LOWER ALKYLAMINO ALKANOLS AND QUATERNARY LOWER ALKYL SALTS THEREOF

The invention described herein was made in the course of work under a grant or award from the Department of Health, Education and Welfare.

SUMMARY OF THE INVENTION

The novel compounds of the present invention have the following formula

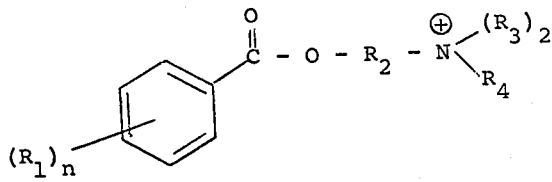

wherein $R_1$ is haloloweralkyl or formyl,
$R_2$ is lower alkylene, or loweralkyl loweralkylene,
$R_3$ is lower alkyl,
$R_4$ is hydrogen or lower alkyl, and where $R_3$ and $R_4$ are both alkyl, they may be the same or different,
X is an anion suitably halide such as chloride, bromide, or iodide, or $SO_4{}^{--}/_2$, and
$n$ is 1 or 2.

The compounds of the present invention are prepared by the route illustrated in the following flow diagram.

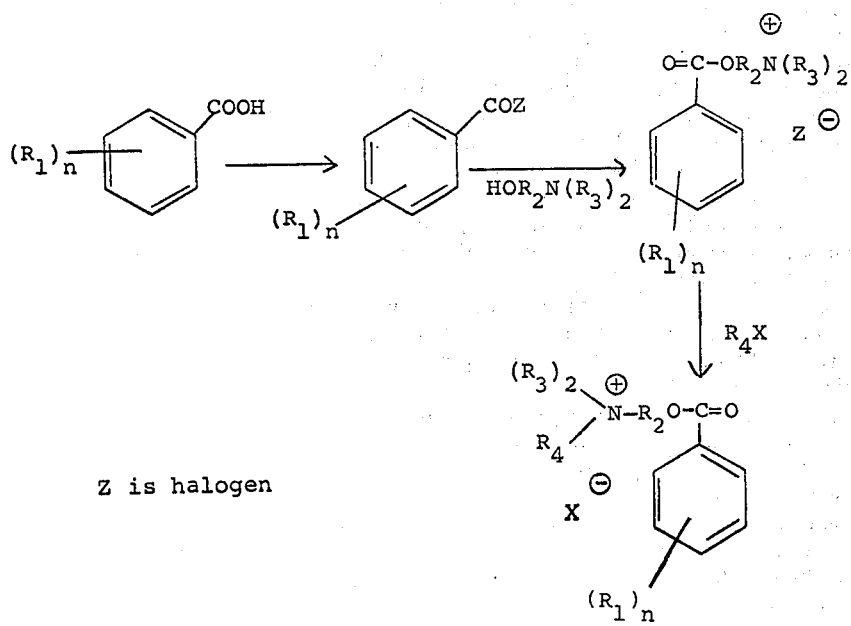

z is halogen

In this procedure, starting with the haloalkyl benzoic acid, the carboxylic acid group is then converted into the corresponding acid halide suitably the acid chloride and reacted with the appropriate dialkyl amino alkanol to form the corresponding ester, suitably in the form of the hydro-halide salt corresponding to the halogen of the acid halide employed. Where it is desired to form the appropriate quaternary salt, the thus produced ester is treated with the appropriate alkyl halide or dialkyl sulfate in the usual manner. The formyl benzoyl ester corresponding to either the dialkyl amino alkyl ester or the quaternary ester is produced by reacting the corresponding halo methyl derivative with dimethylsulfoxide in the presence of sodium bicarbonate. Where 2 halo methyl groups are present on the aromatic nucleus, both will be converted to the corresponding formyl derivative. The compounds of the present invention are insecticides which also exhibit cholinesterase inhibitory activity and show a low level of mutagenic activity when tested against certain microorganisms. It has further been found that alcoholic solutions of the compounds loose their insecticidal activity within approximately 48 hours. It has further been noted that, on a milligram per kilogram scale, the compounds of the present invention are considerably more lethal to insects than to mammals. This combination of properties confers considerable ecological interest upon the compounds of the present invention.

The deterioration of the compounds into non-insecticidal forms after a comparatively short period of time when exposed to hydrophilic solvents substantially eliminates the serious problem of pesticide residue in large scale spraying. Furthermore, the enhanced activity against insects reduces the risk of negatively affective livestock present in the area sprayed. Furthermore, the comparatively low mutagenic activity of the compounds substantially reduces the risk of breeding insect strains which are resistant to these novel compounds.

DESCRIPTION OF THE PREFERRED EMBODIMENTS

The compounds of the present invention possess the following general structure:

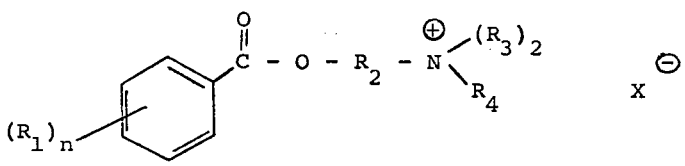

R₁ is formyl or alpha haloalkyl wherein the halo group is suitably chloro, bromo or iodo and the alkyl moiety contains between 1 and 6 carbon atoms, and may be straight-chain or branched, especially preferred however are those compounds wherein R₁ is halo methyl.

R₂ is alkylene or alkyl substituted alkylene wherein the group R₂ contains between 2 and 6 carbon atoms. Especially preferred however are compounds wherein R₂ is ethylene, propylene, isopropylene and isobutylene.

R₃ is lower alkyl containing between 1 and 6 carbon atoms, however those compounds wherein R₃ contains more than 1 carbon atom are not favored due to their decreased solubility.

R₄ is alkyl containing between 1 and 6 carbon atoms, however compounds wherein R₄ contains more than 2 carbon atoms are not preferred due to their decreased solubility. R₄ may also be hydrogen.

Most preferred among the compounds of the present invention are those wherein R₃ and R₄ are both methyl. X, the counter ion, may be any anion which does not interfere with the alkylating function of the whole compound. Thus, for example, carbonate and phosphate are not favored, whereas halide suitably chloride, bromide, or iodide or sulfate may be utilized. n is 1 or 2.

The starting materials utilized in the process of the present invention are the appropriate haloalkylor di(-halo alkyl)-benzoic acids, for example, ortho-, meta-, or para-bromo methyl benzoic acid, 2,3-,2,4-,2,5-,2,6-,3,4-,3, 5- dibromomethyl-, diodomethyl-, or dichloro methylbenzoic acids, ortho-, meta-, or para-alphabromoethyl-, alphachloropropyl, and alpha-iodobutyl benzoic acids, and 2,3-di (alpha-bromopropyl)benzoic acid, and the like.

The appropriate benzoic acid is then converted into the corresponding acid halide, suitably the chloride or bromide by methods known to the art, especially suitable is reaction with thionyl chloride. In the preferred modification a large excess of thionyl chloride is added to the acid and the mixture heated under reflux with stirring until the acid is entirely dissolved. The mixture is then heated under reflux for a further 30 to 60 minutes, the reaction vessel sealed and permitted to cool in an anhydrous atmosphere. The excess thionyl chloride is removed by evaporation under reduced pressure, suitably by use of a rotary evaporator. The acid halide thus produced is not further purified to reduce risk of hydrolysis and is stored in vacuo until utilized in the next stage of the reaction which is the formation of the appropriate dialkylamino alkyl benzoate ester.

Among the dialkylamino alkanols which may be used in this step of the procedure are dimethylamino ethanol, dimethylamino propanol, dimethylamino isopropanol, dimethylamino butanol, dimethylamino isobutanol, dimethyl amino t-butanol and dimethylamino t-amyl alcohol. The corresponding diethyl-, dipropyl- and dibutylamino alkanols may also be employed, however, the dimethylamino alcohol is the reagent of choice in view of the desired solubility of the end-product.

The reaction between the dialkylamino alkanol and the benzoyl chloride is carried out in a solvent preferably a polar solvent, which should however be free of labile hydroxy groups. The solvent of choice is dry chloroform. However, it should be noted that commercially available chloroform contains ethanol as a preservative. This is removed by treating the commercial chloroform with concentrated sulphuric acid, followed by saturated sodium bicarbonate and distilled water. The chloroform is then filtered through magnesium phosphate and stored in the dark over calcium chloride.

In the process of the reaction, the appropriate benzoyl acid halide is dissolved in the solvent, cooled in an ice bath and agitated, the dialkylamino alkanol is taken up in a similar solvent and added dropwise to the cooled stirred system. It has been found that the reaction is most efficient when equimolar amounts of the reactants are present. The product obtained probably exists in the form of the hydrohalide salt corresponding to the halide moiety of the acid halide initially employed. If desired, the anion present may be replaced by another anion by treatment with aqueous alkali, extraction into a suitable solvent and addition of the requisite amount of alternate acid. However, there is no reason for so proceeding. The dialkylamino alkyl haloalkyl benzoate is isolated from the solvent by evaporation under reduced pressure.

Where it is desired to produce the corresponding quaternary ammonium salt the reaction product from the immediately previous stage is not isolated but rather an excess of the appropriate alkylating agent is added to the solution. While any alkylating agent containing 1 to 6 carbon atoms may be employed which does not contain a potential anion which would be incompatible with the alkylating function of the total product, it is however preferred to utilize methyl iodide, ethyl bromide, dimethyl sulfate or diethyl sulfate, preferably methyl iodide and di-methyl sulfate are used as the alkylating agents.

The reaction is carried out at ambient temperature, and the quaternary ammonium salt isolated by filtration and purified by recrystallization suitably from absolute ethanol.

Where it is desired to produce the corresponding dialkylaminoalkyl formyl benzoate or trialkylaminoalkyl formylbenzoate quaternary salt, the starting material and an equimolar amount of sodium bicarbonate (per. haloethyl moiety) are suspended in dimethyl sulfoxide and heated in an oil bath at between 100° and 150°, suitably at about 125° until the vigorous effervescence ceases. Heating time is of the order of 5 to 10 minutes. The reaction mixture is cooled and a small amount of water added thereto to dissolve the inorganic precipitate. Addition of ethanol in the cold gives a crystalline precipitate, which, upon isolation and drying in vacuo yields a hygroscopic glassy solid having spectral characteristics in conformity with the structure of the desired formyl derivative.

It should be noted that certain of the compounds prepared in accordance with the present invention have been found difficult to purifiy to the extent necessary to achieve satisfactory elemental analyses. Their structures can however be sufficiently well allocated from their spectral characteristics. Furthermore, in view of the intended use as insecticides, absolute purity of the material is not essential.

PHYSIOLOGICAL ACTIVITY

As stated heretofore, the compounds of the present invention when tested for inhibition of eel cholinesterase show good activity at rather low concentrations. Inhibition of cholinesterase activity of generally recognized as having positive correlation which insecticidal activity. The results of low concentration testing certain of the compounds of the present invention are shown in the table below. It is of interest to note that the compound listed in the table which at lowest concentrations showed no cholinesterase inhibition was found in field testing to be an extremely potent insecticide against young yellow meal worm adults (*Tenebrio molitor*).

It has further been found in in vitro testing that compounds of the present invention react with DNA but the product appeared to be readily hydrolyzed under very mild conditions.

The compounds of the present invention may be utilized in solid or liquid insecticidal composition such as powder or syrup, the latter may be aqueous solutions or oil based emulsions or the like. The compounds are stable in crystalline form but unstable, insecticidally in the presence of hydroxylic media. Thus any solution or emulsion which is prepared must be used within about 6–10 hours, preferably less in order to maintain high insecticidal activity. Similarly powders should be compounded with non-hydroxylic carriers and maintained in an anhydrous atmosphere.

The concentrations utilized should be between 0.5–100 mg./liter preferably 1–10 mg./liter. Concentrations at the lower end of the scale being satisfactory where immediate contact with the insects to be killed is anticipated.

The compounds are of general insecticidal activity and may be utilized against grubs, beetles, catapillars, moths, aphides and the like. They should not be used to kill insects infesting higher animals, but due to their short effective life, they may be used to disinfect areas generally occupied by higher animals in their absence.

TABLE I

INHIBITION OF ELECTRIC EEL CHOLINESTERASE (TYPE V) BY SUBSTITUTED BENZOYL CHOLINES

Activity Measurement Method: Rappaport et al. Clin. Chim. Acta 4, 227 (1959).

| REAGENT TYPE CONCENTRATION | Bromomethyl- | | Formyl- | |
|---|---|---|---|---|
| | $10^{-6}M$ | $10^{-4}M$ | $10^{-4}M$ | $10^{-3}M$ |
| ortho | None | None | None | None |
| meta | None | None | None | 60% |
| para | None | Complete | None | Complete |
| 2,3 | None | 40% | 50% | Complete |
| 2,4 | None | Complete | 50% | Complete |
| 2,5 | None | 80% | 50% | Complete |
| 3,4 | 30% | 90% | 25% | Complete |

TABLE I-continued

INHIBITION OF ELECTRIC EEL CHOLINESTERASE (TYPE V) BY SUBSTITUTED BENZOYL CHOLINES

Activity Measurement Method: Rappaport et al. Clin. Chim. Acta 4, 227 (1959).

| REAGENT TYPE CONCENTRATION | Bromomethyl- | | Formyl- | |
|---|---|---|---|---|
| | $10^{-6}M$ | $10^{-4}M$ | $10^{-4}M$ | $10^{-3}M$ |
| 3,5 | None | 90% | Complete | Complete |

*Reagent incubated with enzyme at room temperature (22°) for 40 minutes.

EXAMPLE I p-Bromomethyl benzoylchloride p-Bromomethyl benzoic acid (10.5 g., 0.05 moles) is charged to a round-bottom flask equipped with a magnetic stirrer. Thionyl chloride (50 ml.) is added thereto and the mixture heated under reflux with stirring. After approximately 10 minutes the solid material is dissolved. The heating under reflux is continued for an additional 30 minutes, the clear solution stoppered and cooled in a dry atmosphere. The excess thionyl chloride is removed using a rotary evaporator to yield p-bromomethyl benzoyl chloride (m.p. 56°–58°). This product is not further purified but utilized in the next stage of the reaction.

In accordance with the foregoing procedure but where, in place of thionyl chloride there is utilized phosphorus tribromide there is obtained the corresponding p-bromomethyl benzoyl bromide.

EXAMPLE II

Dimethylaminoethyl p-Bromomethyl benzoate

Commercial chloroform is purified by washing with concentrated sulfuric acid, saturated sodium bicarbonate and then distilled water. The chloroform is dried by filtration over magnesium phosphate and stored in a dark bottle over calcium chloride.

p-Bromomethylbenzoylchloride (9.34 g., 0.04 mole) is dissolved in dry chloroform (100 ml.) prepared as above, cooled in an ice bath and stirred magnetically. 2-Dimethylamino ethanol (DMAE) (3.6 g., 0.04 M) is dissolved in dry chloroform (5 ml.) and added dropwise to the solution of the acid chloride with continuous stirring. The reaction mixture remains clear until the last drop of DMAE is added. Evaporation of the chloroform yields dimethylaminoethyl para-bromomethyl benzoate hydrochloride.

Where it is desired to produce the corresponding quaternary salt the product is not isolated but the chloroform solution utilized in the next stage.

EXAMPLE III para-bromomethyl benzoyl choline iodide

To the chloroform solution of Example III is added 30 ml. of methyl iodide. A yellowish flocculant precipitate is formed, the mixture is stirred at room temperature for 15 minutes and the precipitate isolated by filtration. Recrystallization of the residue in absolute alcohol yields para-bromomethyl benzoyl choline iodide m.p. 169°–171°C.

EXAMPLE IV

In accordance with the procedures of Examples I and II but where in place of p-bromomethyl benzoyl chloride there is used as starting material o-bromomethyl benzoic acid
m-bromomethyl benzoic acid
2,3-di(bromomethyl)benzoic acid
2,4-di(bromomethyl)benzoic acid
2,5-di(bromomethyl)benzoic acid
3,4-di(bromomethyl)benzoic acid
3,5-di(bromomethyl)benzoic acid
2,6-di(bromomethyl)benzoic acid
o-alphabromoethyl benzoic acid
m-alphachloropropyl benzoic acid
p-alphabromoisopropyl benzoic acid
2,3-di(alphachloroethyl)benzoic acid there is obtained dimethylaminoethyl o-bromomethyl benzoate
dimethylaminoethyl m-bromoethyl benzoate
dimethylaminoethyl 2,3-di(bromomethyl)benzoate
dimethylaminoethyl 2,4-di(bromomethyl)benzoate
dimethylaminoethyl 2,5-di(bromomethyl)benzoate
dimethylaminoethyl 2,6-di(bromomethyl)benzoate
dimethylaminoethyl 3,4-di(bromomethyl)benzoate
dimethylaminoethyl 3,5-di(bromomethyl)benzoate
dimethylaminoethyl o-alphabromoethyl benzoate
dimethylaminoethyl m-alphachloropropyl benzoate
dimethylaminoethyl p-alphabromoisopropyl benzoate
dimethylaminoethyl 2,3-di(alphachloroethyl)benzoate each in the form of the corresponding hydrochloride salt.

In accordance with the foregoing procedure but where in place of dimethylaminoethanol there is used dimethylaminopropanol, dimethylaminoisopropanol, dimethylamino-t-butanol or dimethylamino-t-amyl alcohol there are obtained the corresponding dimethylaminopropyl-, dimethylaminoisopropyl-, dimethylamino-t-butyl-, and dimethylamino-t-amylhaloalkyl or di(haloalkyl)benzoate hydrochlorides.

EXAMPLE V

In accordance with Exanple IV but where, in place of dimethylaminoethyl p-bromomethyl benzoate, there is utilized dimethylaminoethyl 2,3-di(bromomethyl) benzoate and utilizing bromomethane is place of iodomethane there is obtained 2,3,-di(bromomethyl)benzoyl choline bromide m.p. 125° to 140°.

EXAMPLE VI p-Formyl benzoyl choline bromide. p-Bromomethyl benzoyl choline bromide (102 mg.) sodium bicarbonate (24.8 mg.) and dimethylsulfoxide (0.3 ml.) are heated in an oil bath at 125° for about 5 minutes until vigorous effervescence ceases. The solution is cooled giving a suspension which upon dilution with 2 ml. of water is dissolved. The addition of 5 ml. of absolute ethanol at room temperature yields a crystalline precipitate which is isolated by centrifugation. The solid is isolated, and dried in vacuo at 75° to yield a crisp glassy solid of hygroscopic character having spectral characteristics indicating the structure of p-formylbenzoyl choline iodide. In accordance with the foregoing procedure but starting with o-bromomethylbenzoyl choline iodide
m-bromomethylbenzoyl choline iodide
2,3-di(bromomethyl)benzoyl choline iodide
2,4-di(bromomethyl)benzoyl choline iodide
2,5-di(bromomethyl)benzoyl choline iodide
2,6-di(bromomethyl)benzoyl choline iodide
3,4-di(bromomethyl)benzoyl choline iodide, and
3,4-di(bromomethylbenzoyl choline iodide there is obtained the corresponding o-formylbenzoyl choline iodide
m-formylbenzoyl choline iodide
2,3-diformylbenzoyl choline iodide
2,4-diformylbenzoyl choline iodide
2,5-diformylbenzoyl choline iodide
2,6-diformylbenzoyl choline iodide
3,4-diformylbenzoyl choline iodide
3,5-diformylbenzoyl choline iodide

EXAMPLE VII

In accordance with the procedure of Example III but where, in place of dimethylaminoethyl p-bromomethyl benzoate there is used dimethylaminoethyl o-bromomethyl benzoate
dimethylaminoethyl m-bromomethyl benzoate
dimethylaminoethyl 2,3-di(bromomethyl)benzoate
dimethylaminoethyl 2,4-di(bromomethyl)benzoate
dimethylaminoethyl 2,5-di(bromomethyl)benzoate
dimethylaminoethyl 2,6-di(bromomethyl)benzoate
dimethylaminoethyl 3,4-di(bromomethyl)benzoate
dimethylaminoethyl 3,5-di(bromomethyl)benzoate
dimethylaminoethyl o-alphabromoethyl benzoate
dimethylaminoethyl m-alphachloropropyl benzoate
dimethylaminoethyl p-alphabromoisopropyl benzoate
dimethylaminoethyl 2,3-di(alphachloroethyl)benzoate there is obtained o-bromomethyl benzoyl choline iodide
m-bromomethyl benzoyl choline iodide
2,3-di(bromomethyl)benzoyl choline iodide
2,4-di(bromomethyl)benzoyl choline iodide
2,5-di(bromomethyl)benzoyl choline iodide
2,6-di(bromomethyl)benzoyl choline iodide
2,4-di(bromomethyl)benzoyl choline iodide
3,5-di(bromomethyl)benzoyl choline iodide
o-alphabromomethyl benzoyl choline iodide
m-alphachloropropyl benzoyl choline iodide
p-alphabromoisopropyl benzoyl choline iodide
2,3-di(alphachloroethyl)benzoyl choline iodide

We claim:

1. A compound having the formula

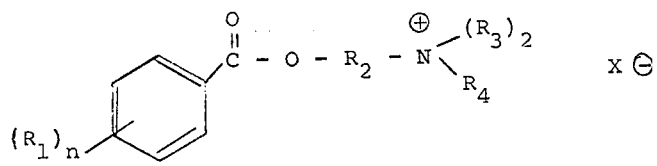

wherein
R₁ is a (monohalo)loweralkyl containing 1–6 carbon atoms or formyl,
n is 1 or 2,
R₂ loweralkylene or loweralkyl loweralkylene wherein the moiety contains 2–6 carbon atoms,
R₃ is loweralkyl of 1–6 carbon atoms,
R₄ is loweralkyl of 1–6 carbon atoms, and
X is halide or sulfate.

2. A compound according to claim 1 wherein
R₁ is monohalomethyl,
R₃ is methyl,
R₄ is hydrogen or methyl,
X is chloride, bromide, or iodide or sulfate.

3. A compound according to claim 2 wherein R₁ is chloromethyl, bromomethyl or iodomethyl and R₂ is ethylene.

4. A compound according to claim 1 wherein
R₁ is formyl,
R₂ is ethylene,
R₃ is methyl,
R₄ is methyl or hydrogen, and
X is chloride, bromide, iodide or sulfate.

5. A compound of claim 1 having the formula

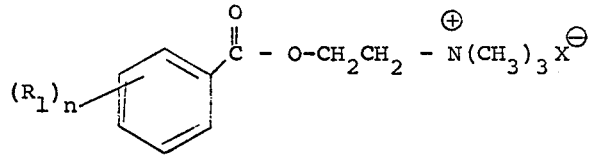

wherein (R₁)ₙ is
o-bromomethyl,
m-bromomethyl,
p-bromomethyl,
2,3-di(bromomethyl),
2,4-di(bromomethyl),
2,5-di(bromomethyl),
2,6-di(bromomethyl),
3,4-di(bromomethyl),
3,5-di(bromomethyl),
or 3,5-di(bromomethyl),
and X is bromide or iodide.

6. A compound of claim 1 having the formula

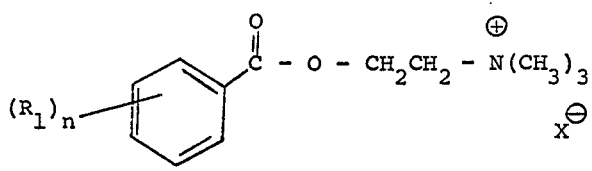

wherein
(R₁)ₙ is
o-formyl
p-formyl
m-formyl
2,3-diformyl, 2,4-diformyl, 2,6-diformyl
2,5-diformyl, 3,4-diformyl
or 3,5-diformyl
and
X is bromide or iodide.

7. A compound having the formula:

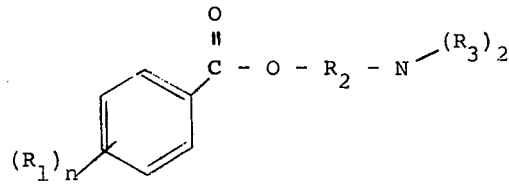

wherein
R₁ is -monohaloloweralkyl containing 1–6 carbon atoms or formyl,
n is 1 or 2,
R₂ is loweralkylene or loweralkyl loweralkylene wherein the moiety contains 2–6 carbon atoms,
R₃ is loweralkyl of 1–6 carbon atoms, and
X is halide.

8. A compound of claim 7 having the formula:

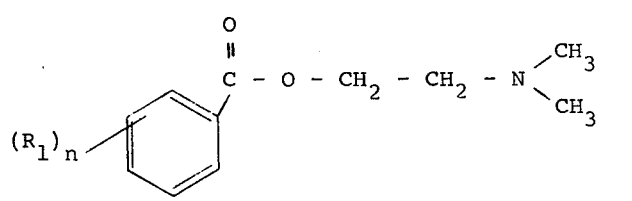

wherein (R₁)ₙ is
o-formyl
p-formyl
m-formyl
2,3-diformyl, 2,4-diformyl, 2,6-diformyl
2,5-diformyl, 3,4-diformyl
or 3,5-diformyl
and
X is bromide or iodide.

9. A compound of claim 7 having the formula

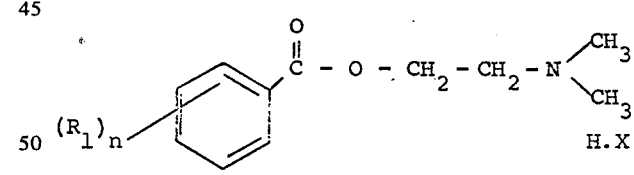

wherein (R₁)ₙ is
o-bromoethyl,
m-bromomethyl,
p-bromomethyl,
2,3-di-(bromomethyl),
2,4-di(bromomethyl),
2,5-di(bromomethyl),
2,6-di(bromomethyl),
2,4-di(bromomethyl),
or 3,5-di(bromomethyl),
and X is bromide or iodide.

* * * * *